(12) United States Patent
Ros et al.

(10) Patent No.: US 9,050,128 B2
(45) Date of Patent: Jun. 9, 2015

(54) CANNULA INSERTER

(75) Inventors: Jérôme Da Ros, Thonon les Bains (FR); Frédéric Neftel, Lausanne (CH)

(73) Assignee: DEBIOTECH S.A., Lausanne (CH)

( * ) Notice: Subject to any disclaimer, the term of this patent is extended or adjusted under 35 U.S.C. 154(b) by 0 days.

(21) Appl. No.: 14/002,852

(22) PCT Filed: Mar. 2, 2012

(86) PCT No.: PCT/IB2012/050994
§ 371 (c)(1),
(2), (4) Date: Sep. 5, 2013

(87) PCT Pub. No.: WO2012/117379
PCT Pub. Date: Sep. 7, 2012

(65) Prior Publication Data
US 2013/0338594 A1 Dec. 19, 2013

(30) Foreign Application Priority Data
Mar. 3, 2011 (EP) .................................... 11156889

(51) Int. Cl.
*A61B 17/34* (2006.01)
*A61M 25/02* (2006.01)
(Continued)

(52) U.S. Cl.
CPC ............ *A61B 17/3415* (2013.01); *A61M 25/02* (2013.01); *A61M 25/0631* (2013.01);
(Continued)

(58) Field of Classification Search
CPC ............ A61M 5/178; A61M 25/0606; A61M 25/0631; A61M 25/02; A61B 17/3417
USPC ............. 604/164.01, 164.04, 164.08, 164.12, 604/174, 177, 192, 198, 263
See application file for complete search history.

(56) References Cited

U.S. PATENT DOCUMENTS 7,850,652 B2 * 12/2010 Liniger et al. ............ 604/164.08
8,568,367 B2 * 10/2013 Griffiths et al. ............... 604/240
(Continued)

FOREIGN PATENT DOCUMENTS

EP 1 970 083 9/2008
EP 1 970 084 9/2008
(Continued)

OTHER PUBLICATIONS

International Search Report for PCT/IB2012/050994, mailed Oct. 2, 2012.
(Continued)

*Primary Examiner* — Theodore Stigell
*Assistant Examiner* — Amber Stiles
(74) *Attorney, Agent, or Firm* — Nixon & Vanderhye, PC

(57) ABSTRACT

Cannula inserter comprising a casing with a distal end, intended to be placed in proximity to the skin of a patient, and an opposite proximal end, a piston fixed at least temporarily by retaining means, drive means designed to exert a propulsion force of the piston in the direction counter to the trigger, and release means intended to release the piston; the inserter additionally comprising a needle fixed to a support; the piston being mounted in the casing in such a way that, once released, it reaches and remains temporarily in a first position, then a second position; the needle and its support also being arranged so as to be able to be driven by the piston in a direction corresponding to the main orientation of the casing, before the piston reaches said first position, and so as to be able to effect an automatic rotation about an axis perpendicular to said main orientation during the movement of the piston between said first position and said second position.

28 Claims, 16 Drawing Sheets

Figure 1:
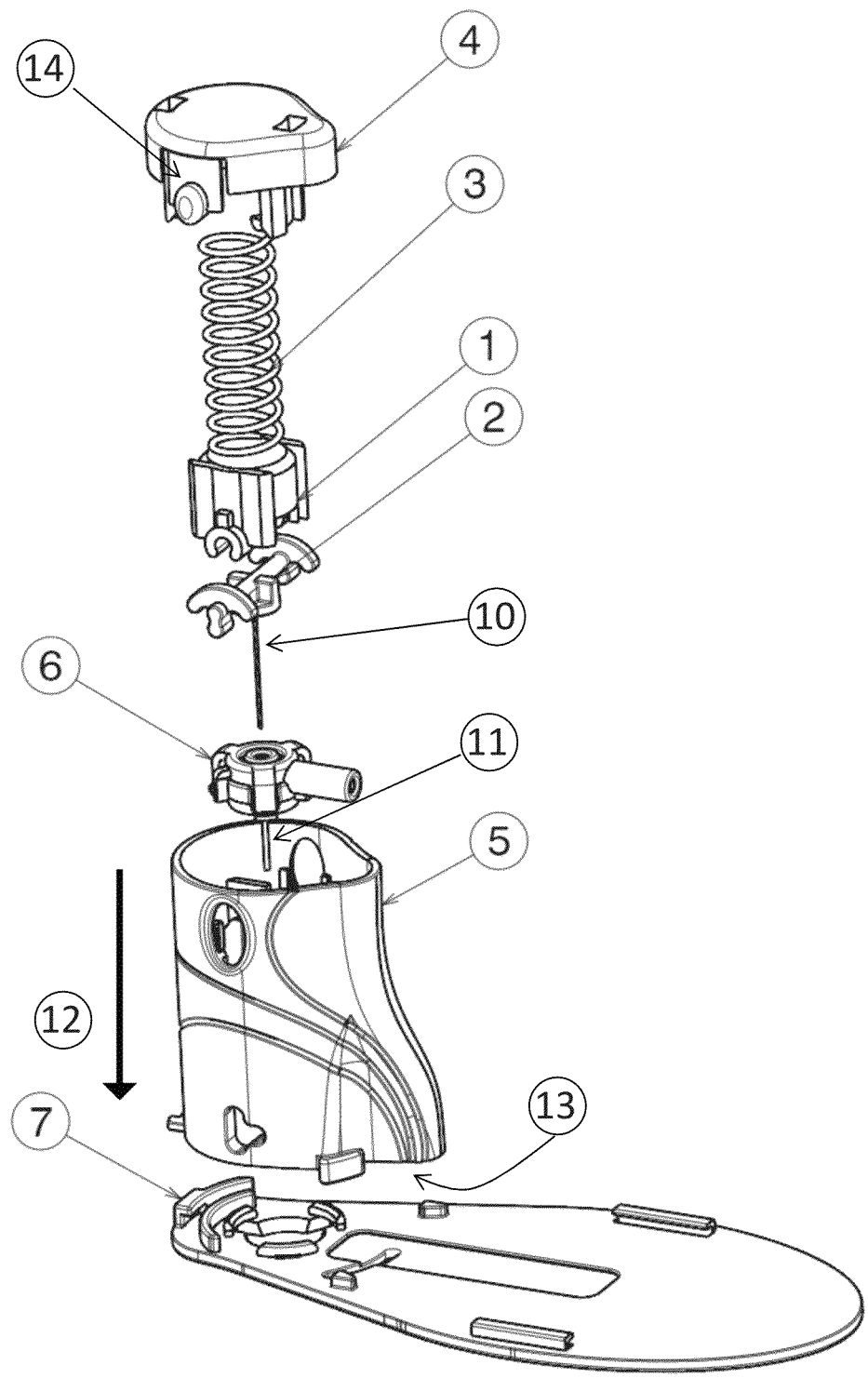

(51) Int. Cl.
*A61M 25/06* (2006.01)
*A61M 5/158* (2006.01)

(52) U.S. Cl.
CPC .......... *A61M25/0606* (2013.01); *A61M 5/158* (2013.01); *A61M 2005/1581* (2013.01); *A61M 2005/1585* (2013.01); *A61M 2005/1587* (2013.01)

(56) References Cited

U.S. PATENT DOCUMENTS

| | | | | |
|---|---|---|---|---|
| 2005/0101912 | A1* | 5/2005 | Faust et al. | 604/117 |
| 2010/0152665 | A1* | 6/2010 | Hasted | 604/164.12 |
| 2011/0046456 | A1* | 2/2011 | Hordum et al. | 600/309 |
| 2012/0029385 | A1* | 2/2012 | Chong et al. | 600/583 |

FOREIGN PATENT DOCUMENTS

| | | |
|---|---|---|
| EP | 1 970 091 | 9/2008 |
| FR | 2 752 164 | 2/1998 |

OTHER PUBLICATIONS

Written Opinion of the International Searching Authority for PCT/IB2012/050994, mailed Oct. 2, 2012.

International Preliminary Report on Patentability(IPRP Chapter I) and English Translation issued Sep. 3, 2013 for applicant's PCT/IB2012/050994 dated Mar. 2, 2012.

* cited by examiner

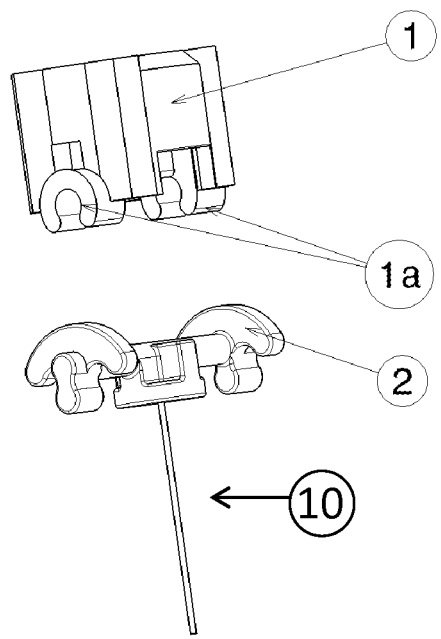
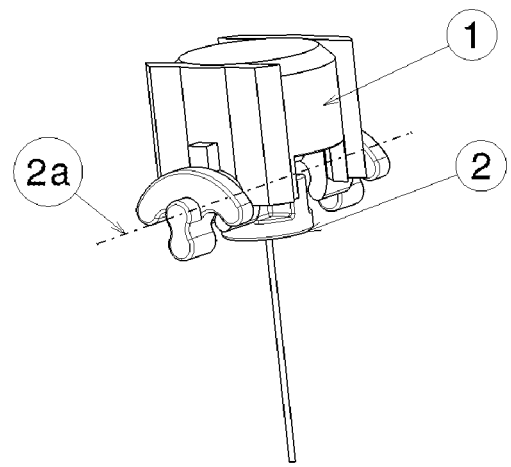
FIG. 2a          FIG. 2b

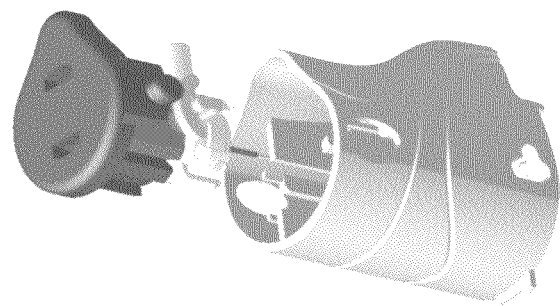
FIG. 13
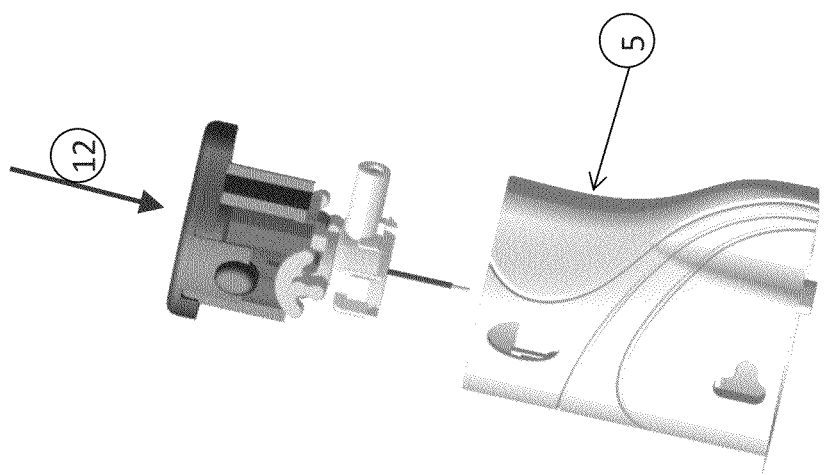

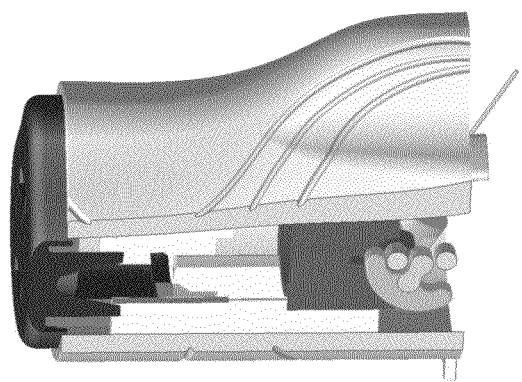
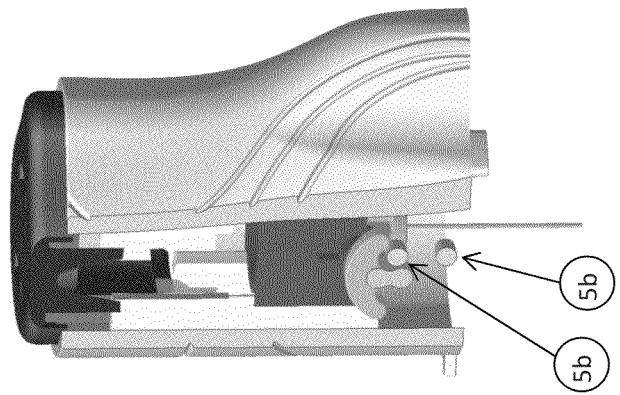
FIG.16

CANNULA INSERTER

This application is the U.S. national phase of International Application No. PCT/IB2012/050994, filed 2 Mar. 2012, which designated the U.S. and claims priority to EP Application No. 11156889.5, filed 3 Mar. 2011, the entire contents of each of which are hereby incorporated by reference.

FIELD OF THE INVENTION

The invention concerns the transdermal insertion and the fixing of a cannula prior to the administration and/or the aspiration of a liquid through the cannula.

PRIOR ART

A cannula inserter as described in EP 1 743 667 A2 or U.S. Pat. No. 6,607,509 B2 comprises a substantially cylindrical body in the interior of which a piston moves. By moving towards the distal end of the inserter, the piston drives the cannula and also a needle—acting as a mandrin—which is disposed in the interior of the cannula. Once the cannula has been put in place, the needle is withdrawn.

The insertion of the cannula and the withdrawal of the needle constitute two important actions in the functioning of a cannula inserter.

In the inserters of the prior art, these two actions are carried out independently of one another. The insertion can be manual, whereas the withdrawal of the needle is automatic, or vice versa.

To date, a sufficiently economical system does not exist permitting these two actions to be combined, in particular when one wishes to insert the cannula at a relatively great speed, which would offer the advantage of simplifying the set, reducing the intervention time and increasing safety. Furthermore, the inserters of the prior art do not permit a cannula to be inserted and fixed easily on a patch and/or such a function to be carried out by means of a device which is sufficiently economical to be designed as single-use.

It is therefore highly desirable to have a cannula inserter which remedies the above-mentioned disadvantages.

GENERAL DESCRIPTION OF THE INVENTION

One of the aims of the present invention is to offer the user the possibility of carrying out the double operation "insertion of the cannula-needle set" and "protection of the needle" by means of the same trigger element, preferably with single-use. The invention permits the use of the inserter by the patient to be simplified by minimizing the number of manipulations, which brings the following advantages: reduction of the risk of errors and reduction of the size of the device.

This aim is obtained owing to the inserter which is the object of the attached claims.

Cannula inserter comprising a casing with a distal end, intended to be placed in proximity to the skin of a patient, and an opposite proximal end, a piston fixed at least temporarily by retaining means, drive means designed to move the piston in the direction counter to the trigger, and release means intended to release the piston; the inserter additionally comprising a needle fixed to a support; the piston being mounted in the casing in such a way that, once released, it reaches and remains temporarily in a first position, then a second position; the needle and its support also being arranged so as to be able to be driven by the piston in a direction corresponding to the main orientation of the casing, before the piston reaches said first position, and so as to be able to effect an automatic rotation about an axis perpendicular to said main orientation during the movement of the piston between said first position and said second position.

In the present specification, the term "cannula" designates a tube intended to be introduced at least in part in the body of the patient so as to permit the passage of liquids, in particular of insulin for diabetic patients.

The driving means can be constituted by a spring or by an elastic or by elastic blades.

The driving means can be composed of a single energy source.

Preferably, the driving means are propulsion means arranged between the piston and the trigger. In another embodiment, the driving means can be traction means arranged between the piston and the distal end of the inserter.

The inserter is preferably ready to use, thus the propulsion means can be pre-loaded and the insertion elements in vertical position housed in the casing.

Safety elements can be arranged either on the proximal end or on the distal end of the inserter. These safety elements can be present in the form of covers or caps to be removed before the use of the inserter.

According to an embodiment, the distal end of the propulsion means serves as a piston.

Expressed differently, the propulsion means and the piston can form part of the same piece, in particular in an embodiment comprising elastic blades as propulsion means.

The retaining means of the piston can be arranged at any location permitting the sought effect to be obtained. Preferably, they are arranged on the trigger. The said retaining means can retain either the piston, for example at its distal end, or the needle support.

The release means of the piston can be arranged at any location permitting the sought effect to be obtained. Preferably, they are arranged on the internal wall of the casing.

The trigger can be present in various ways, for example in the form of one or more buttons which are activatable by the user. These buttons can be positioned in the axis or perpendicular to the inserter.

Preferably, the inserter comprises a safety element which prevents any accidental activation of the trigger. The safety element can be present in the form of one or two buttons arranged on the lateral face of the casing. By depressing the button or buttons, the trigger is no longer retained, so that its activation is possible. In another embodiment, the safety elements are combined with the trigger, so that by depressing simultaneously the safety element or elements and the trigger, the triggering is effective.

The trigger and the safety buttons are preferably arranged so that the inserter is able to be used by a single hand.

Alternatively, the trigger is released by deformation of the casing.

The cannula and its support can be moved in different ways. Advantageously, the piston includes a distal face intended to exert exclusively a thrust effect on the cannula and its support. In this variant, therefore no retaining means (e.g. clips) exist, which would fix the cannula and its support to the piston.

Still within the scope of this variant, the cannula and its support are fixed solely to the needle. This manner of fixing can be obtained by friction, between the needle and a septum arranged in the cannula.

The insertion of the cannula is carried out by an action, namely a pressure on the trigger with possibly, as previously indicated, the prior triggering of a security which retains the trigger. The retraction (rotation) of the used needle is preferably carried out automatically after its withdrawal from the cannula.

The inserter is withdrawn manually. When and/or once the withdrawal has been carried out, the propulsion means move the piston in the main orientation towards its second position, which has the effect of bringing about a rotary movement of the needle.

During the withdrawal, the cannula remains in place in the patient owing to retaining means arranged on its support and a patch previously installed on the patient's skin, or owing to an adhesive integral with the cannula support.

Preferably, the casing includes a protective space in which the retracted needle is housed, and retention means which prevent any inverse rotation of the said needle. Preferably, these retention means are ensured by the residual force of the propulsion means.

Principally, the inserter according to the invention comprises the following elements: a casing, a trigger, a piston, driving means and a needle, this latter being preferably overmoulded in a plastic element, the proximal part of this element constituting the needle support.

The needle support is connected to the piston preferably by a pivot connection.

The trigger contains retention elements permitting a pre-compressed spring to be contained between the piston and the trigger. Preferably, the spring represents the sole source of energy of the inserter.

The cannula is oriented in the main orientation of the casing and is maintained for example by the needle.

The inserter is fixed to the patch owing to retaining means arranged on the said patch, for example by means of a bayonet mechanism or by clips. The trigger has release means from the patch which permits the inserter to separate itself from the patch once the cannula has been inserted. In this configuration, the inserter can advantageously be used as a grip handle facilitating a suitable positioning of the patch on the skin.

In another embodiment, the inserter is placed directly in contact with the patient's skin, and the cannula support has an adhesive tape so as to stick the support on the patient's skin.

Before insertion of the cannula, the needle is guided in the casing to prevent its rotation.

After insertion of the cannula, the stop elements of the casing impart a rotation of the needle and compel it to house itself in the space of the casing provided for this purpose.

Advantageously, the inserter according to the invention comprises safety elements which prevent an inverse rotation of the needle once the latter is housed in the space of the casing provided for this purpose.

Still in a context of safety, the inserter according to the invention can include means which prevent the activation of the trigger as long as the patch is not on the skin.

A pressure on the trigger permits the piston to be released, and also permits the spring to be released, which will translate the piston up to the insertion of the cannula through the patch and the skin. In this first phase, the needle acts as a mandrin which facilitates the insertion of the cannula in the skin.

In a second phase, once the cannula is inserted, the user separates the inserter from the patch by means of a new pressure on the trigger, which permits the retaining means to be released from the patch. The withdrawal of the inserter also brings about the withdrawal of the needle from the cannula, the latter remaining inserted in the patient. During this operation, the piston continues its course in the direction of the distal end of the inserter. The piston moves because it is driven by the propulsion means which have not yet reached their position of rest. This movement of the piston pushes the inserter away in the opposite direction and facilitates the withdrawal of the inserter. This movement of the piston has the simultaneous effect of releasing the needle from the guides of the casing and impel it to carry out a rotation.

LIST OF FIGURES

The invention will be better understood below by means of some illustrated examples. It is obvious that the invention is not restricted to these embodiments.

Figure 3:
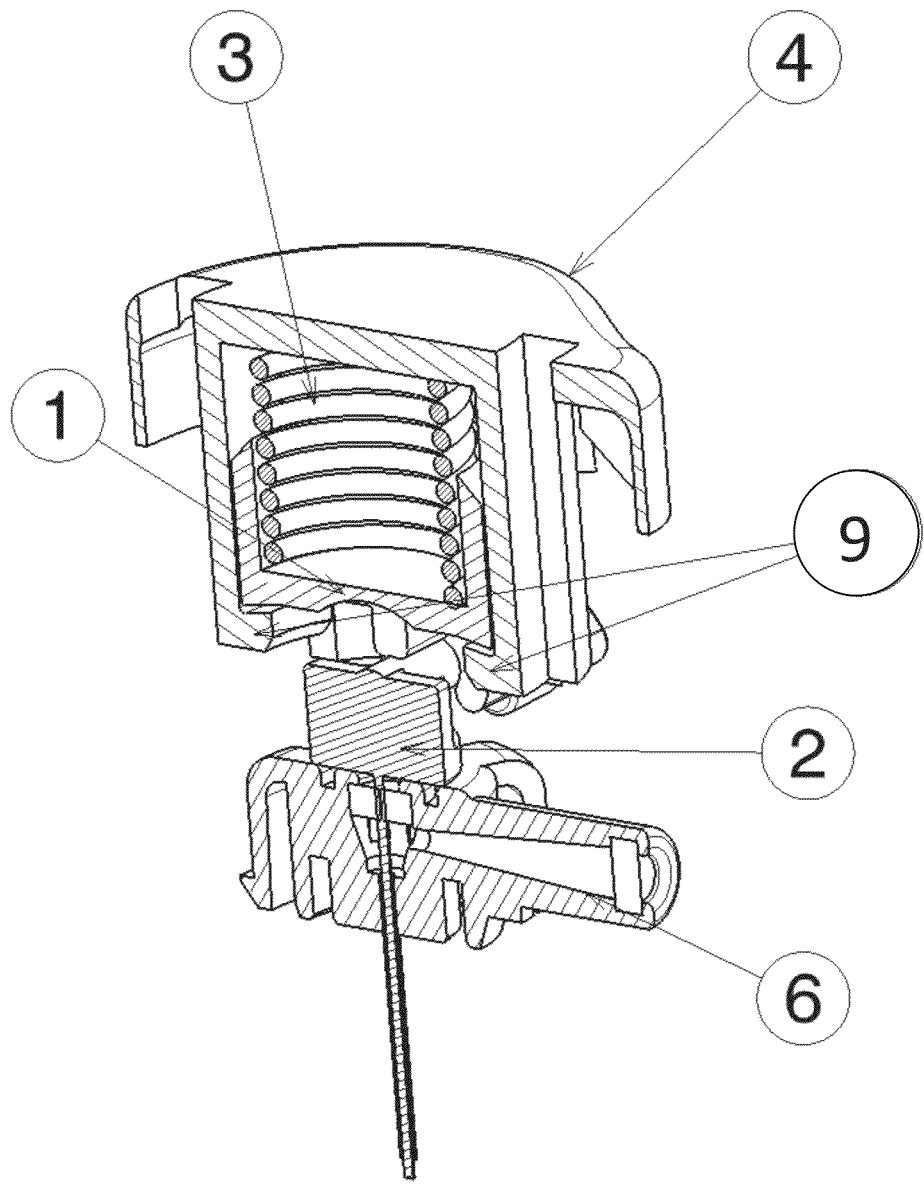
Figure 4:
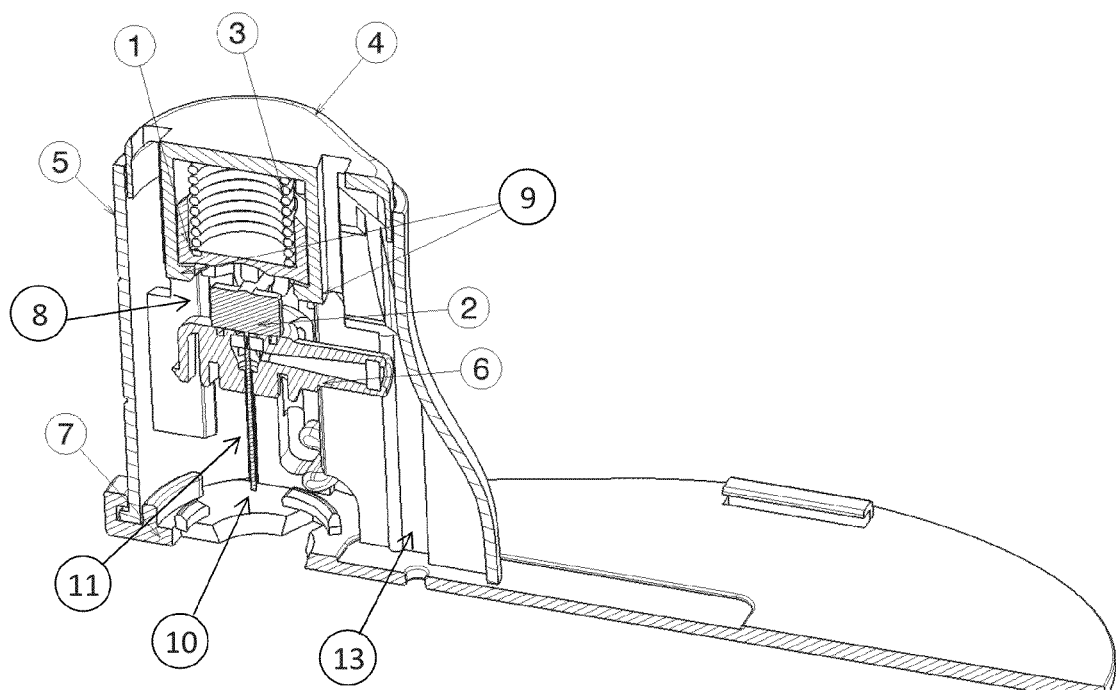
Figure 5A:
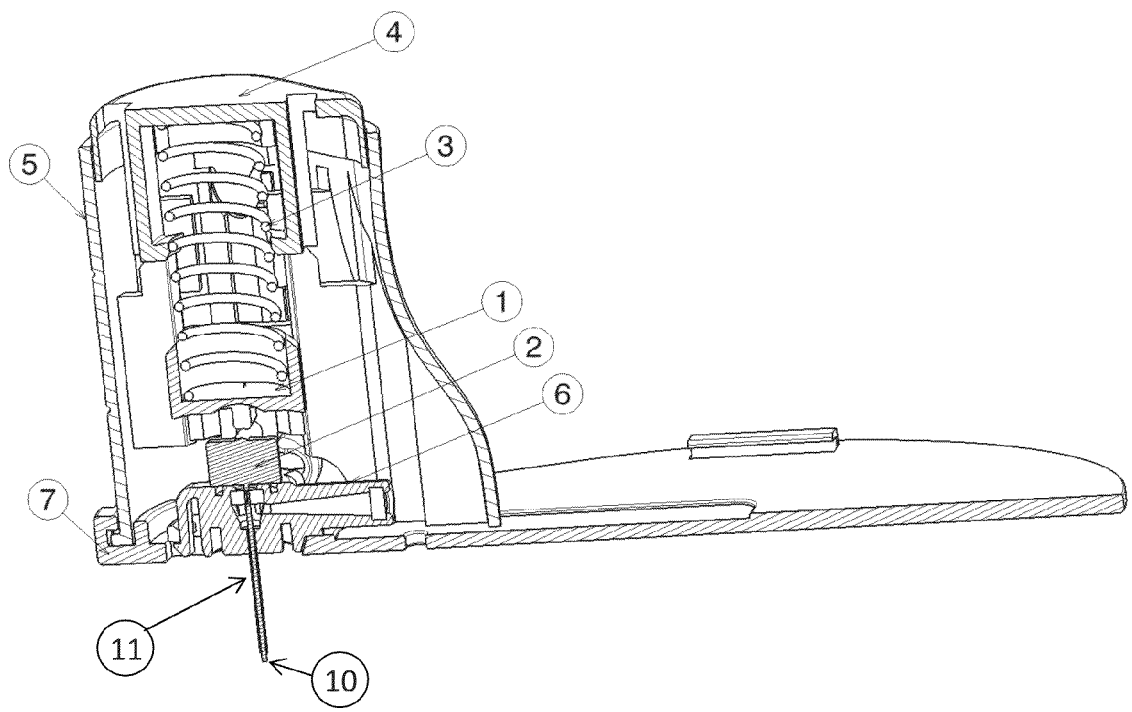
Figure 5B:
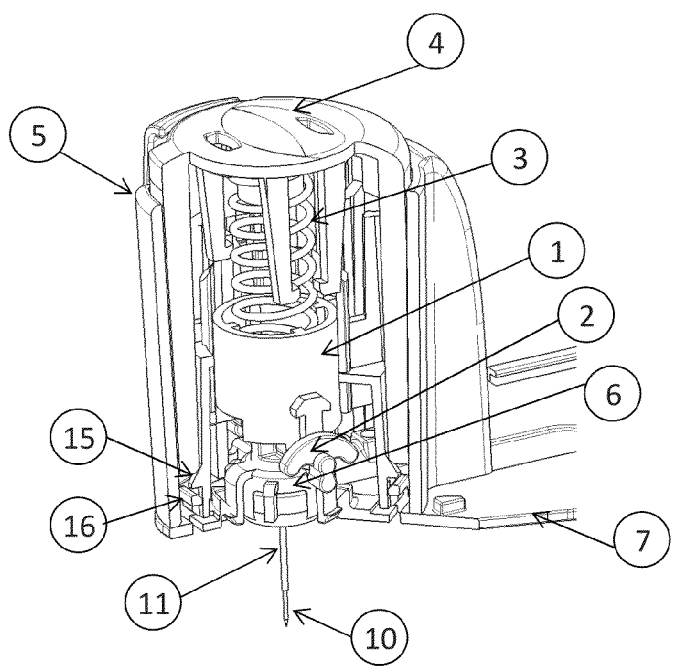
Figure 6A:
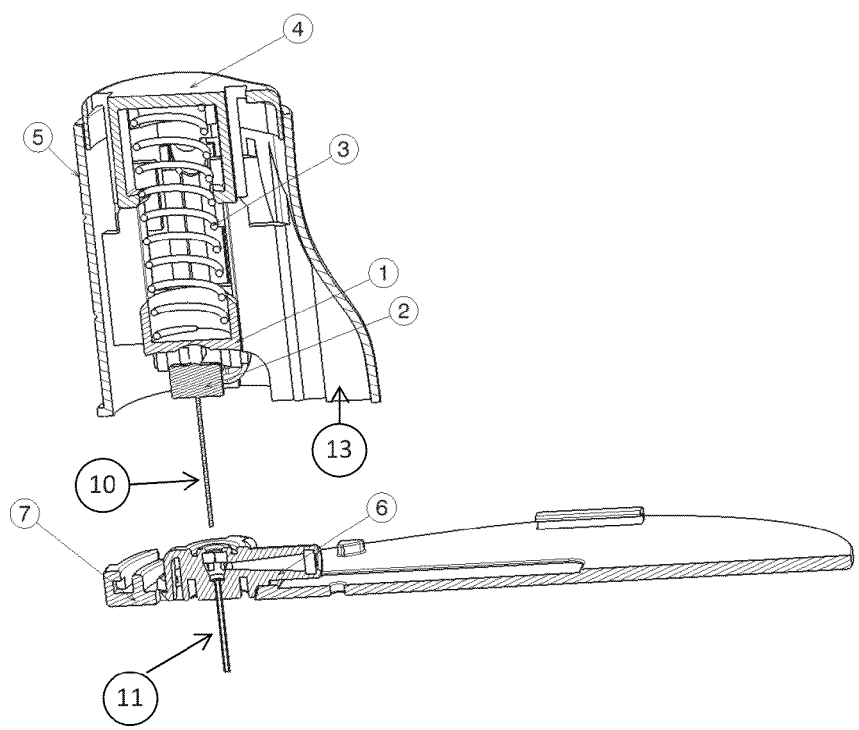
Figure 6B:
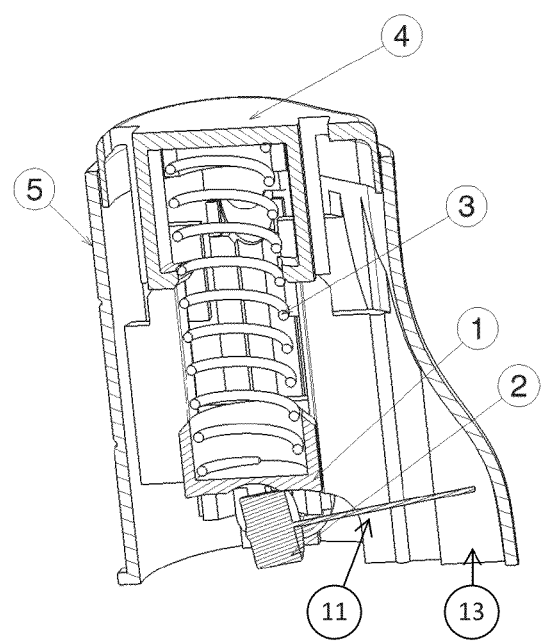
Figure 7A:
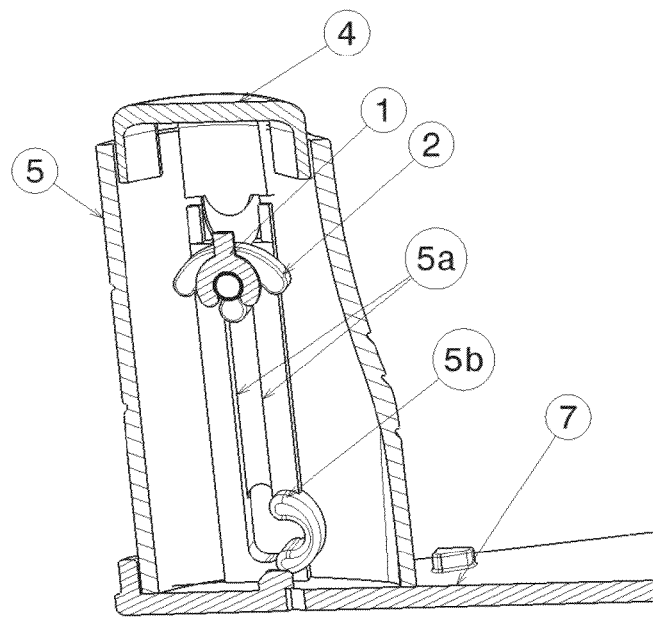
Figure 7B:
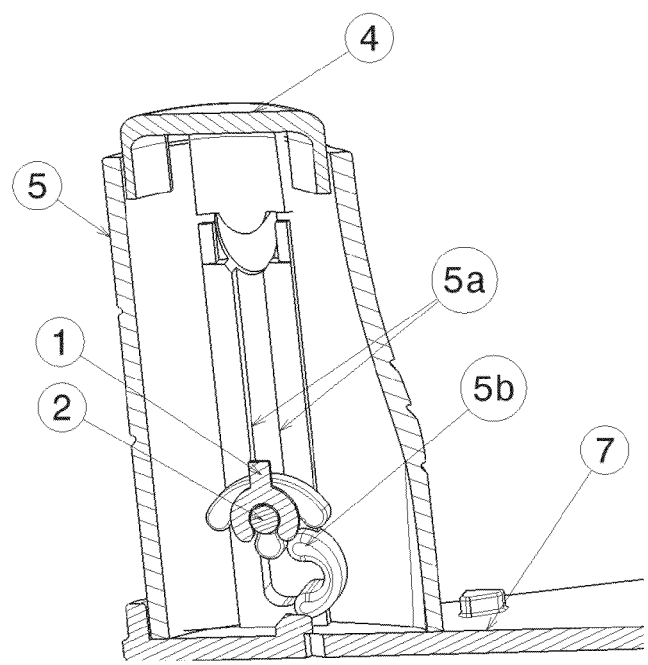
Figure 8A:
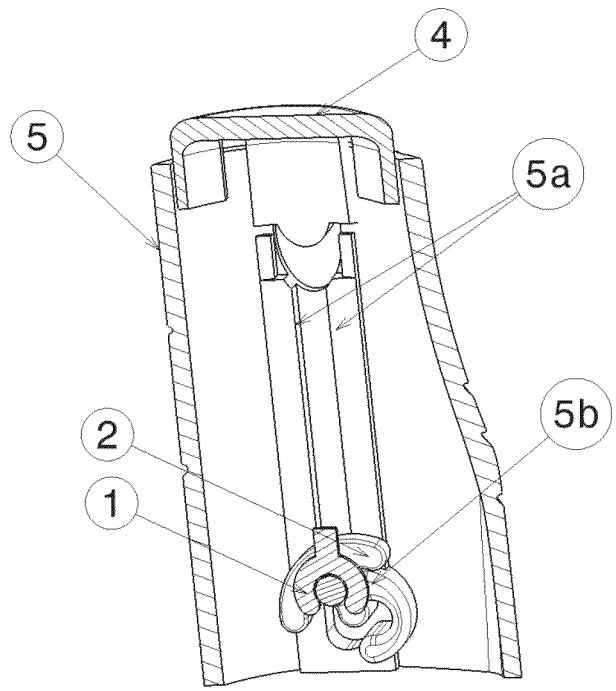
Figure 8B:
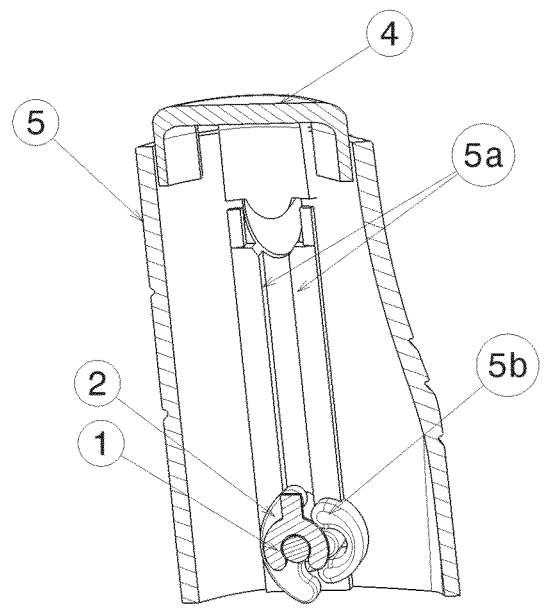
Figure 9:
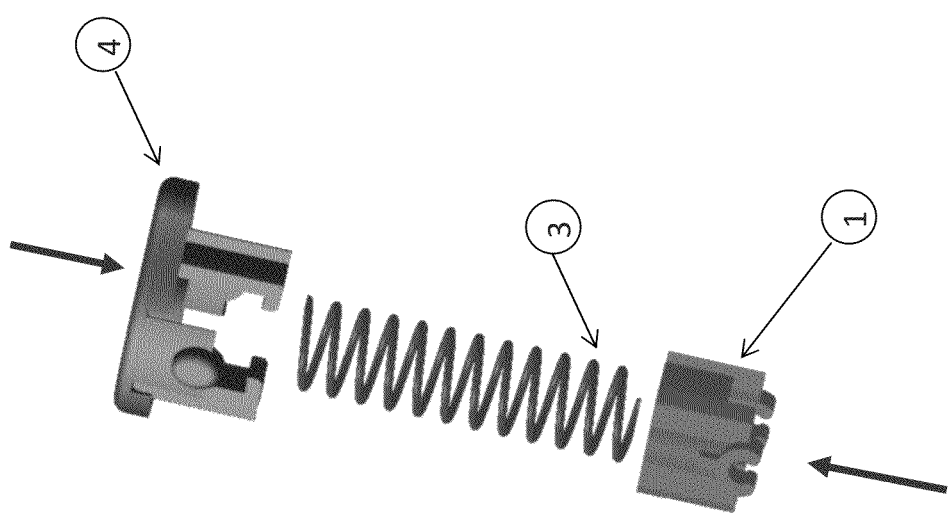
Figure 10:
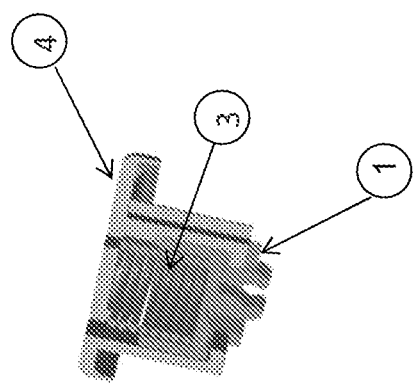
Figure 11:
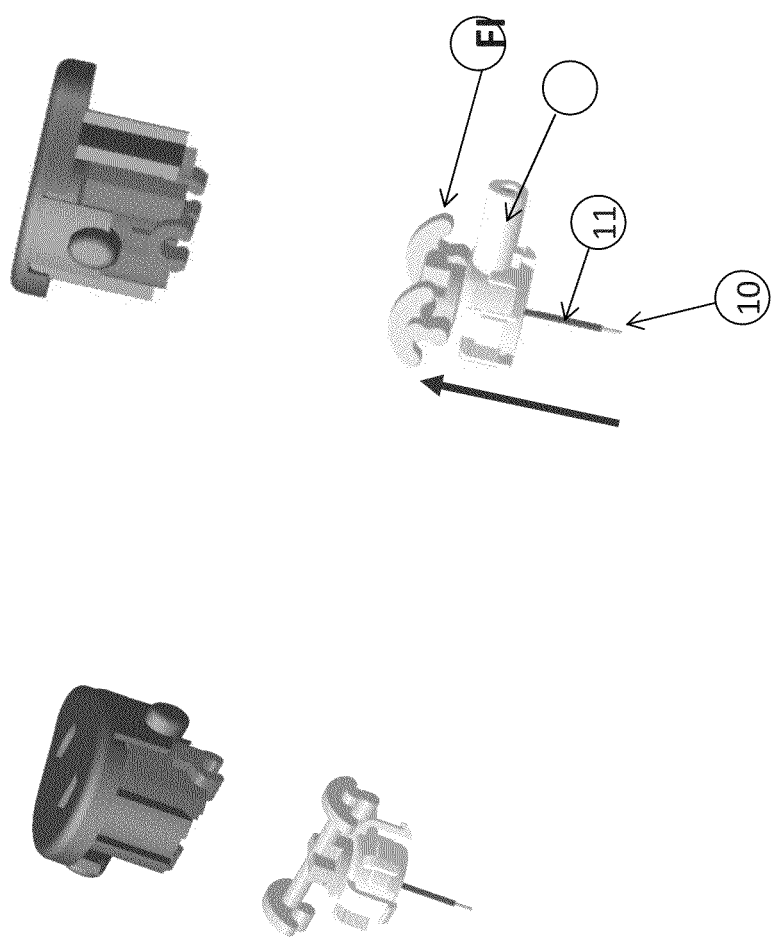
Figure 12:
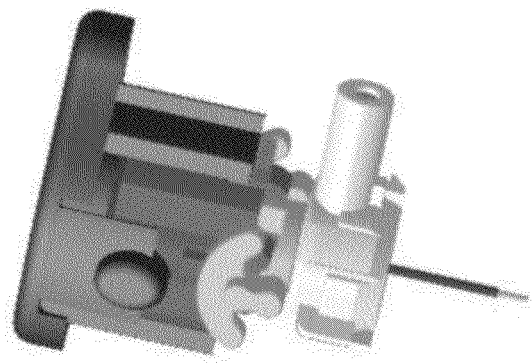
Figure 14:
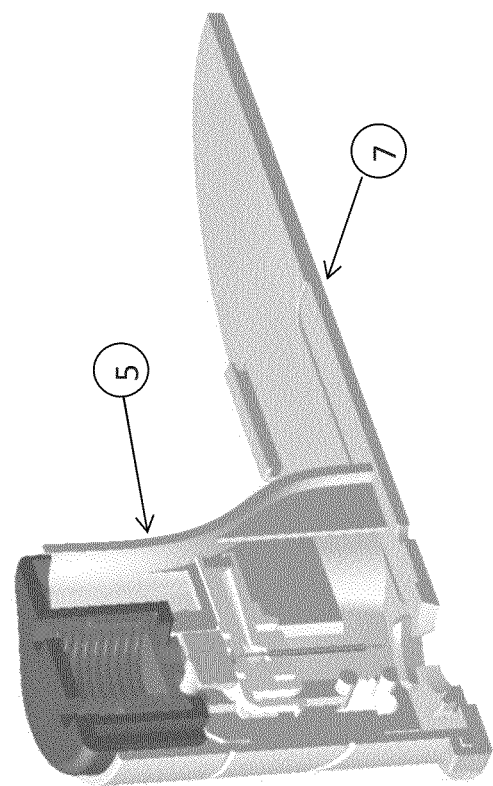
Figure 15:
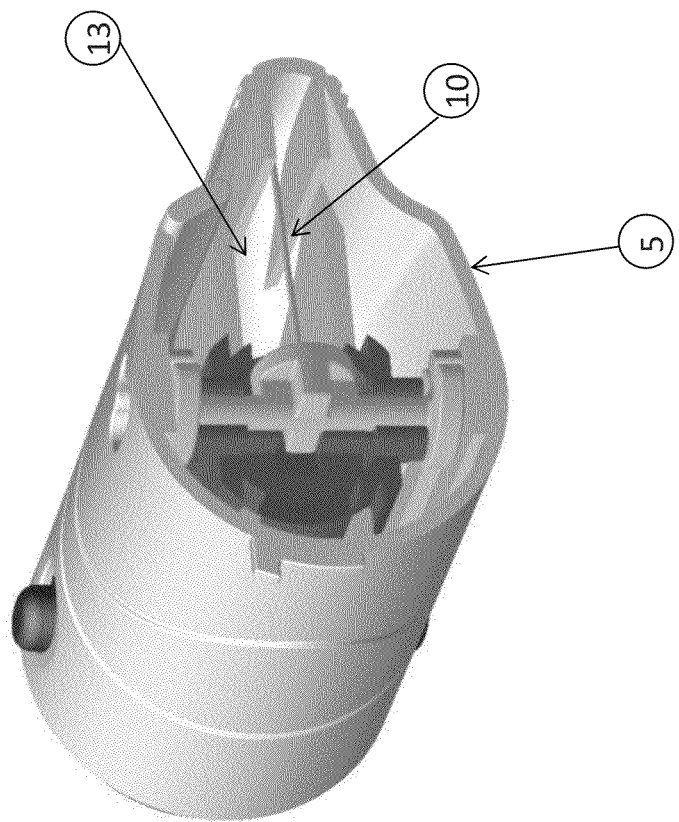

FIG. 1: Set of elements composing the inserter.
FIGS. 2a and 2b: Retaining means of the support of the needle to the piston.
FIG. 3: Armed trigger-piston system.
FIG. 4: Inserter positioned on its patch, before triggering.
FIGS. 5a and 5b: After having actuated the trigger, the cannula and the needle are inserted.
FIGS. 6a and 6b: Withdrawal of the inserter after the cannula has been inserted.
FIGS. 7a and 7b: Path covered by the insertion elements owing to the guide rail.
FIGS. 8a and 8b: Rotation movement carried out by the support of the needle owing to the stops.
FIG. 9: Assembly of the set of piston, trigger and spring.
FIG. 10: Piston-trigger set with the compressed spring.
FIG. 11: Assembly of the piston with the support of the needle.
FIG. 12: Set of the insertion elements with the armed propulsion device.
FIG. 13: Insertion of the trigger-piston-needle-cannula set in the casing.
FIG. 14: Fixing of the inserter on the patch.
FIG. 15: Position of the needle after use.
FIG. 16: Rotation movement of the needle.

DETAILED DESCRIPTION OF THE INVENTION

FIG. 1 represents the different components of the inserter: The piston 1, the needle overmoulded in its support 2, the spring 3, the trigger 4, the casing 5, the cannula 11 and the patch 7. The trigger 4 also comprises at least one safety button 14. The main orientation direction of the casing 12 runs from the proximal end of the inserter to the distal end of the inserter.

FIG. 2 represents the piston 1 with its retention clips 1a permitting the needle support 2 to be clipped, after assembly of the elements, the rotation of the needle support 2 is possible about the axis 2a.

FIG. 3 represents the set of piston 1-trigger 4 with the compressed spring 3 (such that this sub-assembly appears mounted in the casing 5 (cf. FIG. 4)). The retention clips 9 permit the spring 3 to be maintained compressed between the lower piston 1 and the trigger 4.

FIG. 4 represents the inserter in position on the patch 7 before insertion, the retention clips 9 permit the spring 3 to be kept compressed, therefore the inserter is in a stable state. The needle 10 and the cannula 11 are in position ready for the insertion.

Steps of Insertion and Withdrawal

FIG. 4

The spring 3 is pre-compressed and the insertion elements (10 and 11) are in position for the insertion. A pressure on the trigger 4 has the effect of separating the retention clips 9 owing to the release elements 8, and of releasing the piston 1.

FIGS. 5a and 5b

Once triggered, a first release of the spring 3 brings about the insertion of the needle 10 and of the cannula 11 through the patch 7 and the skin of the patient. The cannula support 6 comes to fix itself to the patch 7, for example owing to clips. Thus, the cannula support 6 and the patch 7 become at least temporarily integral. The piston 1, the needle 10 and its support 2 are situated in a temporary position. In this temporary position, the cannula 11 is inserted and the spring 3 remains partly compressed.

A new pressure on the trigger 4 permits the retaining means 16 to be released owing to the release means 15 to separate the inserter 5 from the patch 7.

FIGS. 6a and 6b

Subsequently, during the withdrawal of the inserter, the spring 3 continues to exert an action on the piston 1 which proceeds with its movement towards the distal end of the inserter. This movement induces a displacement of the inserter, in the opposite direction, which facilitates its withdrawal and informs the user that the cannula 11 is inserted. When the needle 10 is withdrawn from the cannula 11, the spring 3 brings about a final displacement of the piston 1 towards its maximum position. In its displacement, which brings it to its maximum position, the piston 1 impels the needle and its support 2 to turn about the axis 2a (FIG. 2b).

Mechanism of Insertion and Rotation of the Needle

FIGS. 7a and 7b

During the insertion phase (represented respectively by FIGS. 7a to 7b), the needle support 2 is guided in the casing 5 owing to the guides 5a to prevent its rotation whilst being maintained by the piston 1.

FIGS. 8a and 8b

After having manually withdrawn the inserter, the action exerted by the spring 3 (FIG. 5a) on the piston 1 brings about its displacement towards the distal end of the casing 5 and pushes the inserter away in the opposite direction. The piston moves a final time to reach its maximum position and consequently the needle support 2 (FIG. 5a) will move against the stop 5b of the casing, therefore, by design, will compel the needle 2 to turn. The used needle is thus set aside in the interior of the inserter so as to protect the patient or any other person handling, or not, the inserter after its use. In particular, the needle is housed in a housing 13 (FIG. 6a) having at least the effect of placing the said needle in safety.

FIG. 16

This figure represents the mechanism of rotation of the needle resulting from the contact between the needle support and stops 5b arranged in the casing.

Fixing of the Cannula on the Patch

The cannula is designed such that it is, for example, clipped to the patch during the insertion phase.

Temporary Fixing of the Piston on the Trigger

This step is illustrated in FIGS. 9 and 10. Once the pieces 4 and 1 are fixed, the spring 3 is compressed between them.

This step during which the spring 3 is compressed can take place before the storage of the inserter or just before its use.

Fixing of the Cannula on the Piston

This step is illustrated in FIGS. 11 and 12.

Insertion of the Set of Trigger-Piston-Needle-Cannula in the Casing

This insertion is illustrated in FIG. 13. It should be noted that the set is inserted at the proximal side of the inserter.

Preferably, the needle and the cannula are arranged in the casing 5 in a direction parallel to the main orientation 12 of the casing 5.

It is, however, also possible to provide a configuration in which these two elements are arranged in a direction which forms a non-zero angle with respect to the main orientation 12 of the casing 5.

Fixing of the Inserter on the Patch

This last step of preparation before the insertion of the cannula is illustrated in FIG. 14. In this example, the inserter is fixed on the patch by means of a bayonet mechanism. In this position, the inserter is ready for use.

Position of the Needle after Use

This final step is illustrated in FIG. 15.

In this example, the needle is directed in a perpendicular direction with respect to the main orientation of the casing.

Finally, it should be noted once again that the invention is not restricted to the examples presented in this application.

Such a cannula can in particular, but not solely, be used for the injection of insulin to a patient by means of a pump coming to be fixed on the patch which comes into fluidic connection with the cannula.

LIST OF NUMERICAL REFERENCES USED IN THE FIGURES 1. piston
1a. retention clips
2. needle support
2a. axis
3. spring
4. trigger
5. casing
5a. guide
5b. stop
6. cannula support
7. patch
8. release element
9. retention clips
10. needle
11. cannula
12. direction of main orientation of the casing
13. needle housing space
14. safety button
15. release element of the inserter
16. retaining element of the patch

The invention claimed is:

1. A cannula inserter comprising:
   a casing with a distal end, intended to be placed in proximity to a patient's skin, and with an opposite proximal end,
   a piston fixed at least temporarily by retaining means,
   drive means designed to move the piston in a direction counter to a trigger,
   release means intended to release the piston,
   a needle fixed to a support,
   wherein the piston is mounted in the casing so that, once the piston is released, the piston reaches a first position,
   wherein the needle and a support of the needle are arranged so as to be able to be driven by the piston in a direction corresponding to a main orientation of the casing, before the piston reaches said first position,
   wherein the piston is mounted in the casing so that the piston remains temporarily in the first position and that the piston reaches and remains temporarily in a second position inside the inserter,
   wherein the needle and the needle support are arranged so as to be able to effect an automatic rotation about an axis perpendicular to said main orientation during the movement of the piston between said first position and said second position, and
   wherein, after said first position, the driving means exert a force in the main orientation so as to drive the piston in the same direction to said second position so as to induce an automatic rotation of the needle and the needle support.

2. The inserter according to claim 1, wherein the driving means are propulsion means arranged between the piston and the trigger.

3. The inserter according to claim 1, wherein the driving means are traction means arranged between the piston and the distal end of the inserter.

4. The inserter according to claim 1, wherein the driving means are a spring, an elastic or an elastic blade.

5. The inserter according to claim 1, wherein the driving means are composed of a single source of energy.

6. The inserter according to claim 1, wherein a spring is pre-compressed.

7. The inserter according to claim 1, wherein a cannula and the needle are in a position ready for an insertion.

8. The inserter according to claim 1, wherein the retaining means are arranged on the trigger.

9. The inserter according to claim 1, wherein the release means are arranged on an internal wall of the casing.

10. The inserter according to claim 1, wherein the trigger is a button which is able to be activated by a user.

11. The inserter according to claim 1, wherein the inserter is designed to be used by a single hand of a person.

12. The inserter according to claim 1, wherein the casing comprises a retaining means of the trigger, said retaining means being adapted for releasing the trigger consecutively to a deformation of the casing.

13. The inserter according to claim 1, wherein the casing includes a space intended to house said needle integrally when the needle is oriented in a direction which differs from said main orientation, said housing acting as protection of the needle against any unintentional lesion.

14. The inserter according to claim 1, comprising stop elements arranged on the casing and on the needle support, so as to allow an automatic rotation of the needle in a space when the piston moves between said first position and said second position.

15. The inserter according to claim 1, wherein the driving means exert a sufficient force on the piston so as to guarantee the maintaining of the needle in a needle housing.

16. The inserter according to claim 1, comprising a safety element arranged so as to initially retain the trigger.

17. The inserter according to claim 1, wherein the piston includes a distal face intended to exert exclusively a thrust effect on a cannula and a support of the cannula.

18. The inserter according to claim 1, wherein the cannula and a support of the cannula are fixed to the piston during the movement towards the distal end of the casing.

19. The inserter according to claim 17, wherein the cannula and the cannula support are fixed solely to the needle by friction.

20. The inserter according to claim 19, wherein a septum is arranged in the cannula, the fixing between the needle and the cannula being realized by friction between the needle and the septum.

21. The inserter according to claim 1, wherein the casing includes a guiding means for guiding and preventing the accidental rotation of the needle and the needle support during the insertion of the cannula.

22. The inserter according to claim 1, wherein the casing includes a guiding means to guide the movement of a cannula from the proximal end towards the distal end.

23. A set comprising the inserter according to claim 1 and a cannula and a support of the cannula, including an adhesive intended to ensure the set being maintained on the patient's skin.

24. A set comprising the inserter according to claim 1 and a cannula including clips arranged so as to fix the cannula to a patch.

25. A set comprising the inserter according to claim 1 and a cannula, wherein the casing is configured so as to act as a gripping member to facilitate the positioning of a patch on the patient's skin.

26. The set according to claim 25, wherein the trigger has a release means which are able to be activated after insertion of the cannula so as to become released from said patch.

27. A set comprising the inserter according to claim 1, comprising a safety means which prevent the activation of the trigger as long as a patch is not on the patient's skin.

28. A set comprising the inserter according to claim 1, comprising a single-use inserter.

\* \* \* \* \*